(12) United States Patent
Bennett

(10) Patent No.: US 6,902,538 B2
(45) Date of Patent: Jun. 7, 2005

(54) SWAB HOLDER

(75) Inventor: Robert Alfred Bennett, Easton, CT (US)

(73) Assignee: Unilever Home & Personal Care USA, division of Conopco, Inc., Greenwich, CT (US)

(*) Notice: Subject to any disclaimer, the term of this patent is extended or adjusted under 35 U.S.C. 154(b) by 187 days.

(21) Appl. No.: 10/132,889

(22) Filed: Apr. 25, 2002

(65) Prior Publication Data

US 2003/0201199 A1 Oct. 30, 2003

(51) Int. Cl.[7] .......................... A61F 13/15; B65D 85/20
(52) U.S. Cl. ............................ 604/1; 206/361; 206/363
(58) Field of Search .................. 206/204, 205, 206/209, 210, 361, 363, 370, 443; 604/1–3

(56) References Cited

U.S. PATENT DOCUMENTS

| | | | |
|---|---|---|---|
| 3,759,375 A | * | 9/1973 | Nappi .......................... 206/362 |
| 4,718,889 A | | 1/1988 | Blasius, Jr. et al. |
| 4,804,362 A | | 2/1989 | Enzo |
| 5,511,654 A | * | 4/1996 | de la Rocha ............... 206/15.3 |
| 5,660,273 A | * | 8/1997 | Discko, Jr. .................. 206/229 |
| 5,883,649 A | * | 3/1999 | Maeda ......................... 347/55 |
| 2002/0185396 A1 | * | 12/2002 | Mainwaring et al. ........ 206/361 |

* cited by examiner

Primary Examiner—Jim Foster
(74) Attorney, Agent, or Firm—Milton L. Honig

(57) ABSTRACT

A swab assembly is provided which includes a swab fitted with an absorbent material at one end of a stick, and a holder for releasably capturing the swab. The holder includes a connecting bridge area with a central groove traversing along a length direction thereof flanked by first and second gripping wings, the wings being sufficiently flexible to bend between a relatively non-stressed and a stressed position allowing the stick, respectively to be engaged and to be released from the groove.

19 Claims, 1 Drawing Sheet

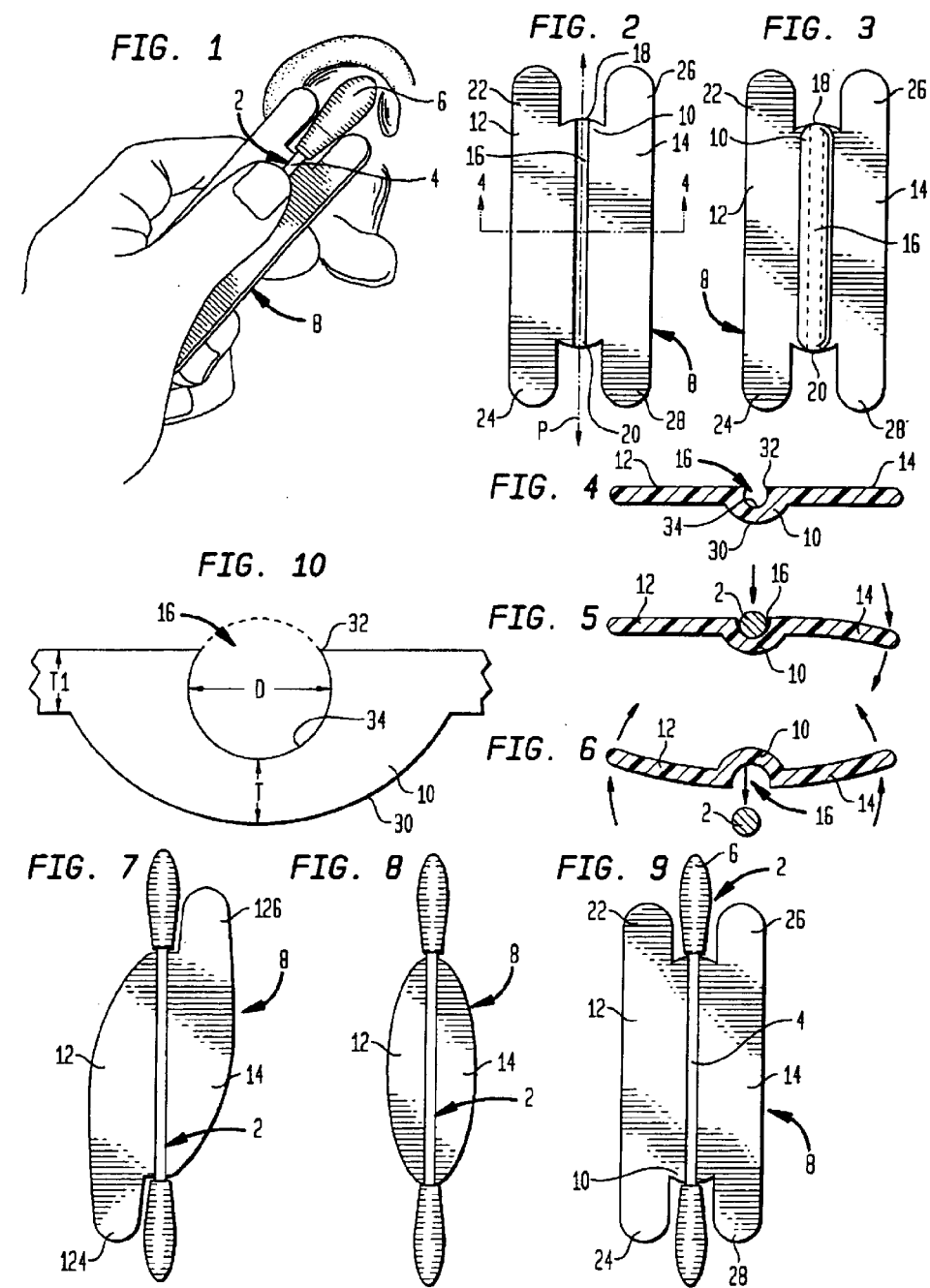

SWAB HOLDER

BACKGROUND OF THE INVENTION

1. Field of the Invention

The invention relates to a device which allows for better, more comfortable gripping of a swab article, particularly a cotton swab stick.

2. The Related Art

Cotton swab sticks have as their major function, cleaning of human ears. In the cleaning process, removal of wax deposits can require the cotton tip to be inserted within a hollow of the ear near the ear drum. Too vigorous a motion may result in puncture or at least some damage to the ear drum. Product configurations have long been sought which would reduce the danger of injury.

U.S. Pat. No. 4,718,889 (Blasius, Jr. et at.) discloses one solution to the problem by providing a resilient cushion element between the end of an applicator stick and the cotton swab tip. Although puncture is minimized by reducing impact against the eardrum, contact is still not avoided.

An alternative direction is taken by U.S. Pat. No. 4,804,362 (Enzo). A stick is provided with a shaped cotton flock including an essentially cylindrical portion having a rounded point and two projecting disc-like portions of different diameters. The disc-like portions are adapted for preventing the rounded point of the cylindrical cleaning portion from contacting the ear membrane. This solution has disadvantages in that the specially molded cotton has poor structural integrity.

Accordingly, it is an advantage of the present invention to provide a swab constructed to avoid damage to the ear in cleaning this body part.

SUMMARY OF THE INVENTION

A swab assembly is provided which includes:
- a swab fitted with an absorbent material attached to an end of a stick; and
- a holder for releasably capturing the swab, the holder including a connecting bridge area with a central groove flanked by first and second gripping wings, the wings being sufficiently flexible to bend between a relatively non-stressed and a stressed position allowing the stick respectively to be engaged and to be released from the groove.

The holder in most embodiments is symmetrical. By this is meant that a plane bisecting the groove is a plane of symmetry. In the preferred embodiments the first and second wings are of substantially identical shape.

Advantageously at least one of the wings further includes a finger projecting beyond a terminal end of the groove along a length direction thereof. In some embodiments the holder includes a set of four fingers, each located at a terminal end of the respective wings. Alternatively, the first and second wings can have respective fingers projecting beyond respective first and second terminal ends of the groove, but the fingers point away from one another in opposite directions.

Preferably the bridge area has a curved surface on a side dorsal to a mouth of the groove. In cross section, this groove will have a circular inner surface with a certain diameter. The curved and inner surfaces are separated by a bridge area thickness. Advantageously, the diameter and thickness have a respective ratio of about 3:1 to about 1:1, optimally about 2:1. A typical cross-section diameter preferably ranges from about 0.04 to about 0.06 inches (0.1 to 0.15 cm), optimally about 0.05 inches (0.13 cm). The diameter of the groove preferably ranges from about 0.092 to about 0.096 inches (0.23 to 0.24 cm), optimally about 0.094 inches (0.24 cm).

Advantageously the bridge area thickness is about equivalent to a thickness found in the wings.

Materials of construction may be any suitably flexible plastic. Particularly preferred is low density polyethylene and polypropylene.

Swabs according to this invention include a stick which at either or both ends is provided with an absorbent tip material. Most suitable is cotton but other types of natural or synthetic fibers may be utilized separately or as blends. Foamed sponges may also be useful as the absorbent material. These typically are formed from polyurethane foam.

Sticks useful herein include those of cellulosic or plastic origin. The sticks may be of wood or can be formed from a tightly wrapped paper stock. Plastics are also suitable as stick material. Representative plastics include polyethylene, polypropylene, polyester and polyamide.

Although the swab assembly of the present invention is particularly suitable for cleaning of the ear, the assembly may be utilized for other purposes. One of these may be for the delivery of colorants to the nails or to paintings. For these, the holder is useful for its grippability.

BRIEF DESCRIPTION OF THE DRAWING

Further advantages and features of the present invention will become more readily apparent from consideration of the drawing in which:

FIG. 1 demonstrates use of the swab assembly for cleaning ears;

FIG. 2 is a top plan view of a first embodiment according to the present invention;

FIG. 3 is a bottom plan view of the first embodiment;

FIG. 4 is a cross-sectional view taken along line 4—4 of FIG. 2;

FIG. 5 is a cross-sectional view similar to that of FIG. 4 except demonstrating the holder engaging a swab captured in the groove;

FIG. 6 is a cross-sectional view wherein the swab assembly of FIG. 5 has been turned 180° and the holder flexed to release the swab;

FIG. 7 is a second embodiment of a holder;

FIG. 8 is a third embodiment of a holder;

FIG. 9 is the first embodiment wherein the holder engages a swab to form the assembly; and FIG. 10 is an enlarged partial cross-sectional view of the connecting bridge area on the holder.

DETAILED DESCRIPTION OF THE INVENTION

FIG. 1 illustrates use of the swab assembly in the cleaning of an ear. The assembly includes a swab 2 constructed with a stick 4 and a cotton tip 6 absorbent material. FIGS. 2, 3 and 9 best illustrate a first embodiment of a holder 8 for releasably capturing the swab. The holder includes a connecting bridge 10 flanked by first and second gripping wings 12, 14. A central groove 16 traverses a length of the connecting bridge. Respective first and second ends 18, 20 define the termini of the central groove.

A plane of symmetry P bisects the groove. On either side of this plane, the shape of the holder is substantially identical.

Gripping wings 12, 14 are formed with respective fingers 22, 24, 26 and 28. These fingers project beyond the respective first and second ends 18, 20.

FIG. 4 illustrates the holder in cross-section without swab. This view best illustrates that the connecting bridge area has a curved surface 30 on a side dorsal to a mouth 32 of the central groove 16.

FIG. 10 provides a more detailed cross-sectional view of the connecting bridge area. Central groove 16 has a circular inner surface 34 with a diameter D. The curved surface 30 and circular inner surface 34 are separated by a bridge area thickness T. In this embodiment, the bridge area thickness T is about equivalent to a thickness T' found along most of the wing area.

FIG. 5 illustrates insertion of a swab into the central groove aided by slight pressure against at least one of the wings. Release of the swab from the holder is best illustrated in FIG. 6. Bending pressure in a direction opposite to that of the groove mouth opens the mouth a sufficient distance to release the swab.

FIG. 7 illustrates a second embodiment of a holder according to the present invention. Herein the fingers 124 and 126 face in opposite directions from one another and are positioned at opposite ends of the holder. The embodiment shown in FIG. 8 utilizes no fingers whatsoever.

Except in the operating and comparative examples, or where otherwise explicitly indicated, all numbers in this description indicating amounts of material ought to be understood as modified by the word "about".

The term "comprising" is meant not to be limiting to any subsequently stated elements but rather to encompass non-specified elements of major or minor functional importance. In other words the listed steps, elements or options need not be exhaustive. Whenever the words "including" or "having" are used, these terms are meant to be equivalent to "comprising" as defined above.

The foregoing description and examples illustrate selected embodiments of the present invention. In light thereof variations and modifications wilt be suggested to one skilled in the art, all of which are within the spirit and purview of this invention.

What is claimed is:

1. A swab assembly comprising:
   a swab fitted with an absorbent material attached to an end of a stick; and
   a holder for releasably capturing the swab, the holder comprising a connecting bridge area with a central groove flanked by first and second gripping wings, the wings being sufficiently flexible to bend between a relatively non-stressed and a stressed position allowing the stick respectively to be engaged and to be released from the groove, and wherein at least one of the wings further comprise a finger projecting beyond a terminal end of the groove along a length direction of the assembly, at least part of the absorbent material projecting beyond the wings and finger in the length direction of the assembly.

2. The assembly according to claim 1 wherein the holder is bisected through the groove by a plane of symmetry.

3. The assembly according to claim 1 wherein the first and second wings are of substantially identical shape.

4. The assembly according to claim 1 wherein the connecting bridge area has a curved surface on a side dorsal to a mouth of the groove.

5. The assembly according to claim 4 wherein in cross-section the groove has a circular inner surface with a diameter, the curved and inner surfaces being separated by a bridge area thickness, the diameter and thickness having a ratio of about 3:1 to about 1:1.

6. The assembly according to claim 5 wherein the ratio of diameter to thickness is about 2:1.

7. The assembly according to claim 5 wherein the connecting bridge area thickness is about equivalent to a thickness found in the wings.

8. A swab assembly comprising:
   a swab fitted with an absorbent material attached to each of a first and a second end of a stick; and
   a holder for releasably capturing the swab, the holder comprising a connecting bridge area with a central groove flanked by first and second gripping wings, the wings being sufficiently flexible to bend between a relatively non-stressed and a stressed position allowing the stick respectively to be engaged and to be released from the groove, and wherein at least part of the absorbent material attached to each of the first and second ends of the stick projects beyond respective first and second gripping wings along a length direction of the assembly.

9. The assembly according to claim 8 wherein the holder is bisected through the groove by a plane of symmetry.

10. The assembly according to claim 8 wherein the first and second wings are of substantially identical shape.

11. The assembly according to claim 8 wherein the connecting bridge area has a curved surface on a side dorsal to a mouth of the groove.

12. The assembly according to claim 11 wherein in cross-section the groove has a circular inner surface with a diameter, the curved and inner surfaces being separated by a bridge area thickness, the diameter and thickness having a ratio of about 3:1 to about 1:1.

13. The assembly according to claim 12 wherein the ratio of diameter to thickness is about 2:1.

14. The assembly according to claim 12 wherein the connecting bridge area thickness is about equivalent to a thickness found in the wings.

15. A swab assembly comprising:
   a swab fitted with an absorbent material attached to both a first and second end of a stick; and
   a holder for releasably capturing the swab, the holder comprising a connecting bridge area with a central groove flanked by first and second gripping wings, the wings being sufficiently flexible to bend between a relatively non-stressed and a stressed position allowing the stick respectively to be engaged and to be released from the groove, and wherein the groove has first and second terminal ends distant from one another, and the first and second wings further comprise respective first and second fingers projecting beyond respective first and second terminal ends resulting in the fingers pointing away from one another, at least a part of the absorbent material on each of the first and second ends of the stick projecting beyond first and second fingers respectively along a length direction of the assembly.

16. The assembly according to claim 15 wherein the holder is bisected through the groove by a plane of symmetry.

17. The assembly according to claim 15 wherein the first and second wings are of substantially identical shape.

18. The assembly according to claim 15 wherein the connecting bridge has a curved surface on a side dorsal to a mouth of the groove.

19. The assembly according to claim 15 wherein the holder is bisected through the groove by a plane of symmetry.

* * * * *